US012605153B2

(12) United States Patent (10) Patent No.: US 12,605,153 B2
Harper et al. (45) Date of Patent: Apr. 21, 2026

(54) RETRACTOR TOOL APPARATUS AND METHOD OF MANIPULATION

(71) Applicant: SeaSpine Orthopedics Corportion, Carlsbad, CA (US)

(72) Inventors: Michael Roscoe Harper, Carlsbad, CA (US); Trevor Thomas Jaye, Carlsbad, CA (US); Sarah Jauregui, Carlsbad, CA (US); Matthew Steven Horner, San Diego, CA (US); Daniel Scott Davenport, Collegeville, PA (US)

(73) Assignee: SeaSpine Orthopedics Corporation, Carlsbad, CA (US)

( * ) Notice: Subject to any disclaimer, the term of this patent is extended or adjusted under 35 U.S.C. 154(b) by 454 days.

(21) Appl. No.: 17/877,021

(22) Filed: Jul. 29, 2022

(65) Prior Publication Data

US 2023/0035781 A1 Feb. 2, 2023

Related U.S. Application Data

(60) Provisional application No. 63/227,850, filed on Jul. 30, 2021.

(51) Int. Cl.
A61B 17/02 (2006.01)

(52) U.S. Cl.
CPC ..................................... A61B 17/02 (2013.01)

(58) Field of Classification Search
CPC ................ A61B 17/02; A61B 17/0206; A61B 17/0218; A61B 17/025; A61B 2017/0256; A61B 1/32
See application file for complete search history.

(56) References Cited

U.S. PATENT DOCUMENTS

| | | | | |
|---|---|---|---|---|
| 6,139,493 A * | 10/2000 | Koros | ................ | A61B 17/0206 |
| | | | | 600/231 |
| 8,974,381 B1 * | 3/2015 | Lovell | .................... | A61B 90/30 |
| | | | | 600/222 |
| 9,615,818 B2 * | 4/2017 | Baudouin | .......... | A61B 17/0218 |
| 10,363,022 B2 * | 7/2019 | Serokosz | ........... | A61B 17/7077 |
| 10,863,975 B2 * | 12/2020 | Rosenbaum | ....... | A61B 17/0206 |
| 2005/0137461 A1 * | 6/2005 | Marchek | .............. | A61B 17/025 |
| | | | | 600/220 |
| 2008/0183046 A1 | 7/2008 | Boucher | | |
| 2012/0203070 A1 | 8/2012 | Crenshaw | | |
| 2013/0190575 A1 * | 7/2013 | Mast | .................. | A61B 17/7079 |
| | | | | 600/219 |

(Continued)

FOREIGN PATENT DOCUMENTS

WO WO-2005096735 A2 * 10/2005 ........... A61B 17/025

OTHER PUBLICATIONS

International Searching Authority; International Search Report and Written Opinion issued in Application No. PCT/US2022/038814; 18 pages; dated Dec. 21, 2022.

(Continued)

*Primary Examiner* — Ellen C Hammond
(74) *Attorney, Agent, or Firm* — Dinsmore & Shohl LLP

(57) ABSTRACT

A retractor tool apparatus and method of manipulation are described. The retractor tool may include one or more blades. The one or more blades may be cranial/caudal blades. The one or more blades may be a medial blade. One or more portions of the retractor tool may be adjustable.

17 Claims, 9 Drawing Sheets

(56) References Cited

U.S. PATENT DOCUMENTS

| | | | |
|---|---|---|---|
| 2019/0015089 A1 * | 1/2019 | Rosenbaum | ....... A61B 17/0206 |
| 2020/0214686 A1 * | 7/2020 | Truckey | ............. A61B 17/0206 |

OTHER PUBLICATIONS

The International Bureau of WIPO; International Preliminary Report on Patentability issued in PCT/US2022/038814 issued on Jan. 18, 2024, 11 pages.

European Patent Office; Invitation to Pay Additional Fees and Partial Search Report issued in PCT App. No. PCT/US2022/038814, 11 pages, dated Oct. 31, 2022.

Chilean First Substantive Report issued in App. No. 202400212 dated Jun. 19, 2025.

Chilean Substantive Report issued in App. No. 202400212 dated Dec. 23, 2025.

* cited by examiner

RETRACTOR TOOL APPARATUS AND METHOD OF MANIPULATION

CROSS-REFERENCE TO RELATED APPLICATIONS

This application is a nonprovisional patent application of and claims priority to and benefit under 35 U.S.C. § 119 to U.S. Provisional Application No. 63/227,850, filed Jul. 30, 2021. The entire contents of the aforementioned application are herein incorporated by reference in its entirety.

TECHNICAL FIELD

The embodiments of the invention are in the field of retractor manipulation.

SUMMARY

In some embodiments of the invention, for example, a retractor tool may include at least one blade. In various embodiments, at least one blade may be adjustable in length.

In addition, in some embodiments, at least one blade may telescope between a first length and a second length longer than the first length. In various embodiments, at least one blade may include an upper blade and a lower blade telescoping relative to each other. In some embodiments, at least one blade may be a medial blade and/or a cranial/caudal blade. In various embodiments, the retractor tool may include a pivoting engagement between a base arm and at least one blade, wherein the pivoting engagement allows at least one blade to angle both in and out from the base arm. In some embodiments, at least one blade may include a joint allowing a first portion of at least one blade to move relative to a second portion of at least one blade, wherein the first portion may be a connector engaging a base arm and the second portion is a remaining portion of at least one blade. In various embodiments, the retractor tool may include a first drive mechanism to both decrease and increase the length of at least one blade. In some embodiments, the retractor tool may include a base rack, wherein the base rack includes a second drive mechanism to both contract and distract a distance between two blades. In various embodiments, the retractor tool may include a base arm and an extension arm extending from the base arm for a variety of lengths. In some embodiments, the retractor tool may include a catch stopping the extension arm extending from the base arm at a predetermined length of the variety of lengths.

In some embodiments, a retractor tool may include a base arm. In various embodiments, the retractor tool may include at least one blade. In some embodiments, the retractor tool may include a pivoting engagement between the base arm and at least one blade allowing at least one blade to angle both in and out from the base arm.

In addition, in some embodiments, the retractor tool may include a drive mechanism to operate the pivoting engagement. In various embodiments, at least one blade may include a joint between a connector and a remaining portion of at least one blade, wherein the joint allows conical movement between the connector and the remaining portion of at least one blade. In various embodiments, the remaining portion of at least one blade may include an upper blade and a lower blade, wherein the lower blade telescopes relative to the upper blade. In some embodiments, the pivoting engagement may include the base arm having a worm gear and at least one blade having a worm wheel. In various embodiments, the retractor tool may include an extension arm extending from the base arm for a variety of lengths. In some embodiments, the retractor tool may include a catch stopping the extension arm extending from the base arm at a predetermined length of a variety of lengths.

In some embodiments, a method of retracting may include providing a retractor tool having a first blade connected to a first base arm and an opposing second blade connected to a second base arm. In various embodiments, the method may include manipulating the first blade by at least one of adjusting a length of the first blade. In some embodiments, the method may include adjusting a distance between the first blade and the second blade. In various embodiments, the method may include adjusting an angle between the first blade and the first base arm.

In addition, in some embodiments, adjusting the distance between the first blade and the second blade may include driving both contraction and distraction of the distance between the first blade and the second blade. In various embodiments, the method of adjusting the length of the first blade may include telescoping an upper blade relative to a lower blade of the first blade. In some embodiments, the method of telescoping may include driving the lower blade away from and/or towards the upper blade. In various embodiments, the method of adjusting the angle between the first blade and the first base arm may include driving the first blade to angle both in and out from the first base arm. In some embodiments, the method may include adjusting a connector of the first blade relative to a remaining portion of the first blade. In various embodiments, the method of adjusting may include about 3 degrees of conical movement of the connector relative to the remaining portion of the first blade. In some embodiments, the method may include locking an extension arm relative to the first base arm at a maximum extension length. In some embodiments, the method may include adjusting a length of the second blade different from the length of the first blade to change access within the retractor tool.

In some embodiments, a retractor system and/or kit may include a retractor tool.

In addition, in some embodiments, the retractor tool may be a medial-based retractor. In various embodiments, the retractor system may include one or more implants. In some embodiments, the retractor system may include one or more screws.

In some embodiments, a retractor tool may include one or more blades.

In addition, in some embodiments, the one or more blades may be a medial-based blade. In various embodiments, the one or more blades may be a cranial/caudal blade. In some embodiments, the tool may include a floating head. In various embodiments, the tool may include threads for telescoping. In some embodiments, the tool may include one or more gears, wherein the one or more gears may include teeth. In various embodiments, the tool may include a table arm lock. In some embodiments, the tool may include one or more illuminators or external light sources. In various embodiments, the one or more blades may contract and/or distract.

In some embodiments, a method of retracting may include a medial-based retractor.

In addition, in some embodiments, the retractor may not directly touch the implant. In various embodiments, the retractor may directly engage the vertebrae to indirectly compress the interbody implant. In some embodiments, the retractor may indirectly engage an interbody implant once the implant is in situ. In various embodiments, the method may include controlling toe-in and/or toe-out of the blades via one or more gears and/or teeth. In some embodiments, the method includes telescoping of one or more blades. In various embodiments, the method may include telescoping of the blades via threads. In some embodiments, the method may include telescoping of a medial blade. In some embodiments, the method may include a table arm lock. In various embodiments, the method may include applying a force via the table arm lock to move the vertebrae in a spondylolisthesis adjustment. In various embodiments, the method may include fixing the retractor tool via the table arm lock.

In some embodiments, a retractor tool may include a floating head or connector.

In addition, in some embodiments, the floating head or connector may allow flexibility of in situ adjustment of blade engagement. In various embodiments, the floating head may engage a worm gear. In some embodiments, the floating head may allow different approach angles in different planes. In various embodiments, the floating head may allow assembly of a modular retractor components.

In some embodiments, a floating head or connector for use with a retractor tool may include a worm gear interface for toeing capability.

In addition, in some embodiments, the floating head may include about 3 degrees of conical movement introduced at a blade head.

BRIEF DESCRIPTION OF THE ILLUSTRATIONS

Embodiments of the invention are illustrated in the following illustrations. Also, the drawings are not necessarily to scale, emphasis instead generally being placed upon illustrating the principles of the invention.

DETAILED DESCRIPTION

Figure 1:
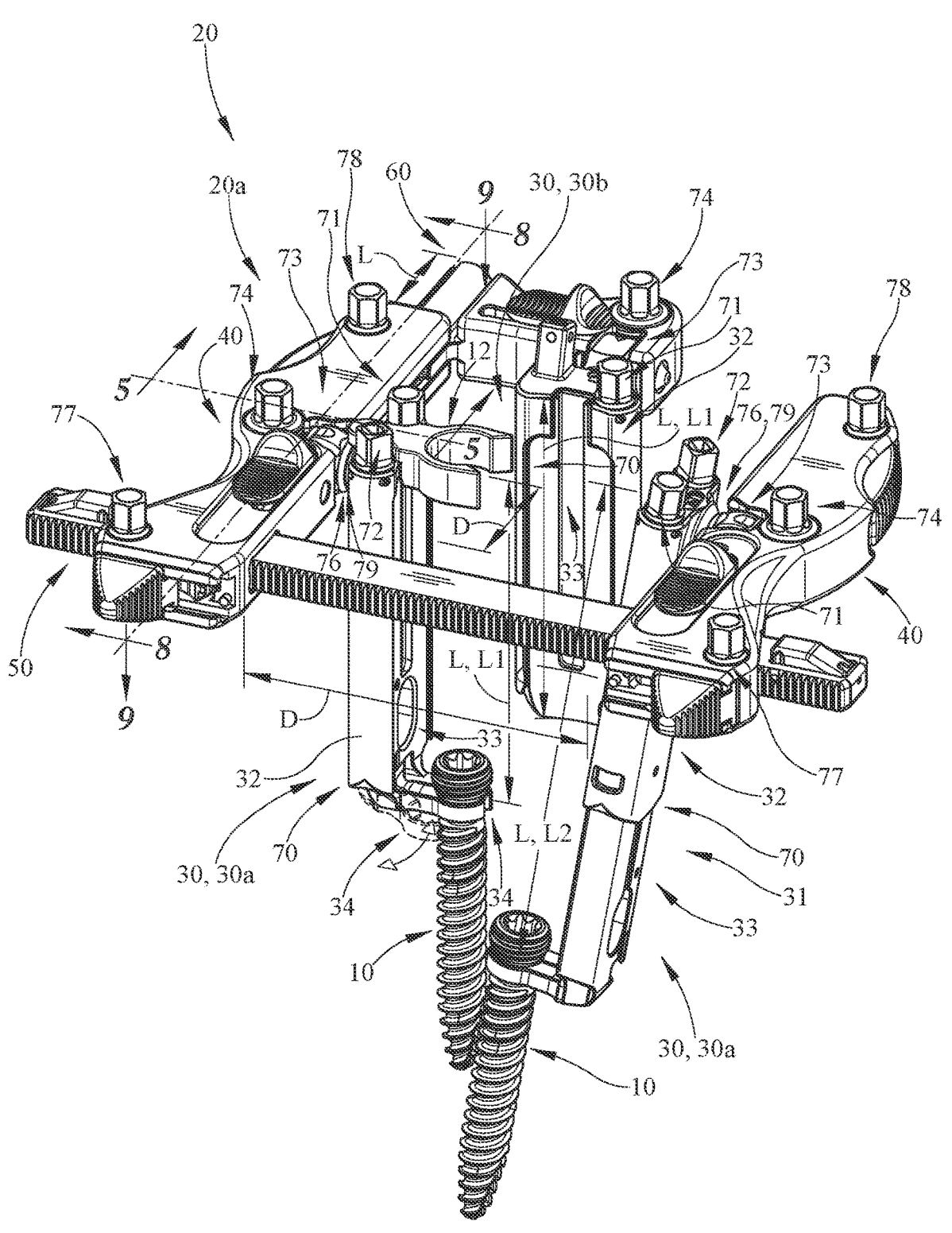
FIG. 1 is a perspective view of one embodiment of a retractor tool illustrating the cranial/caudal blade extended and/or pivoted.
Figure 2:
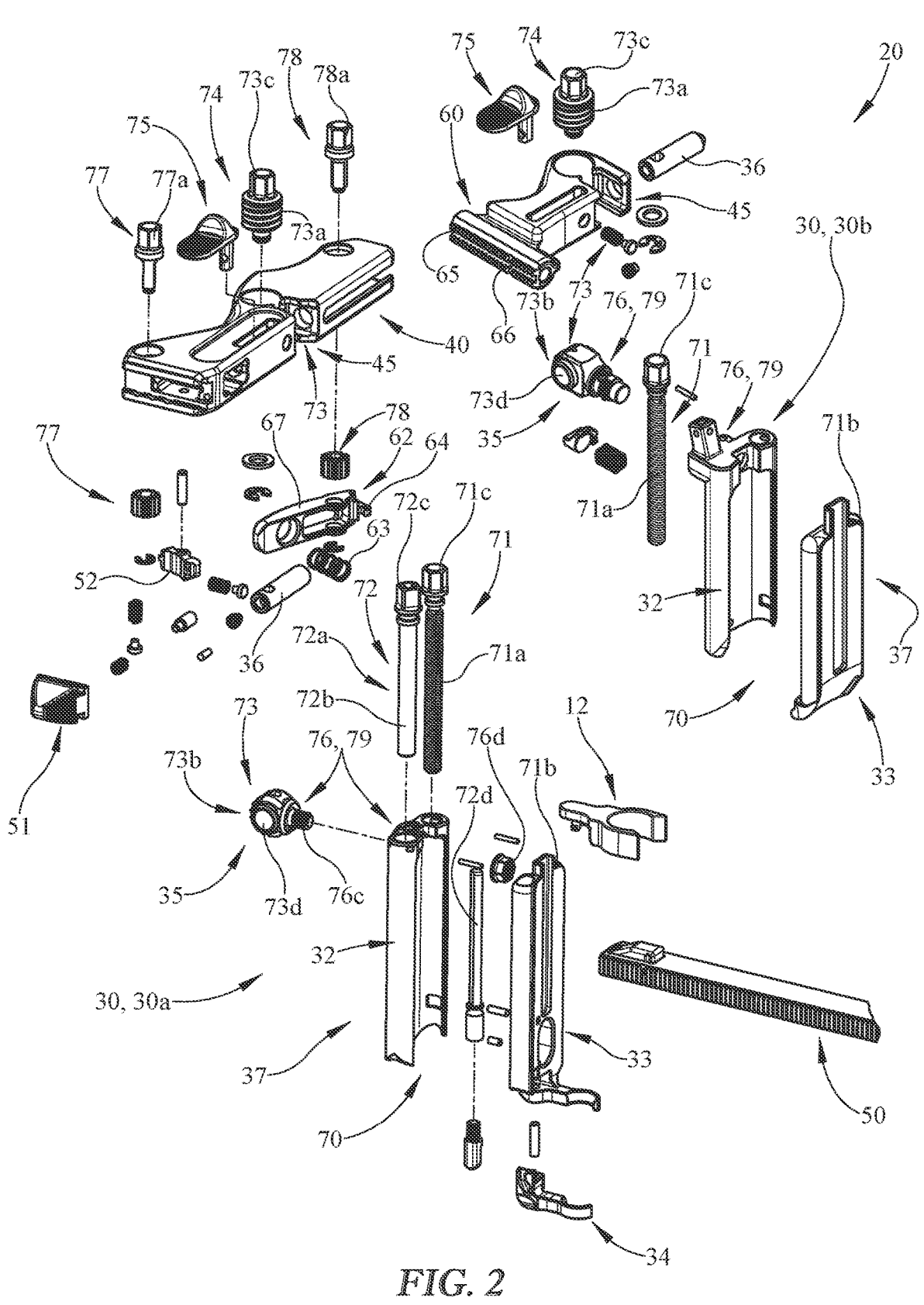
FIG. 2 is an exploded view of a portion the retractor tool of FIG. 1.
Figure 3:
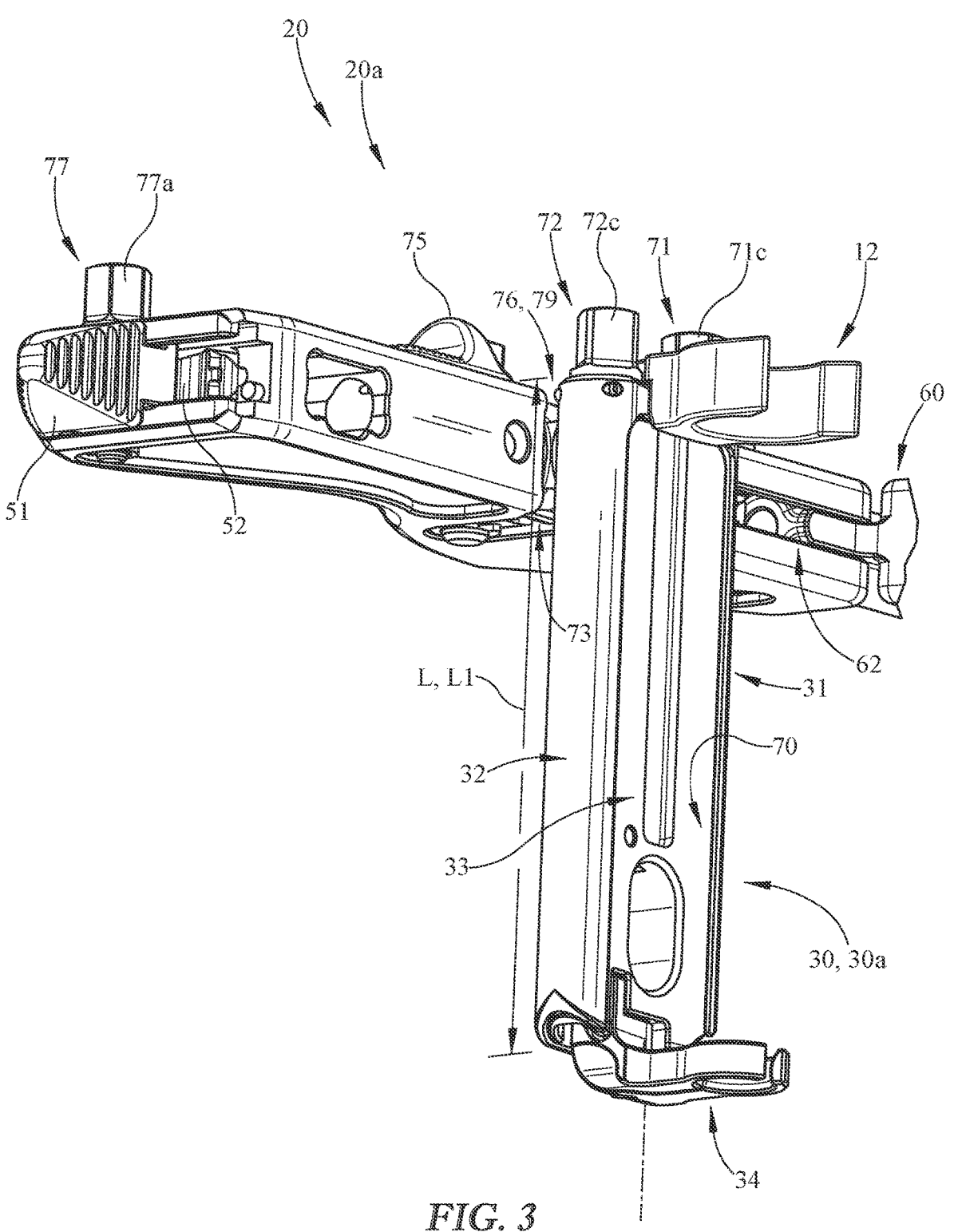
FIG. 3 is a perspective view of the cranial/caudal blade at a first length and the base arm.
Figure 4:
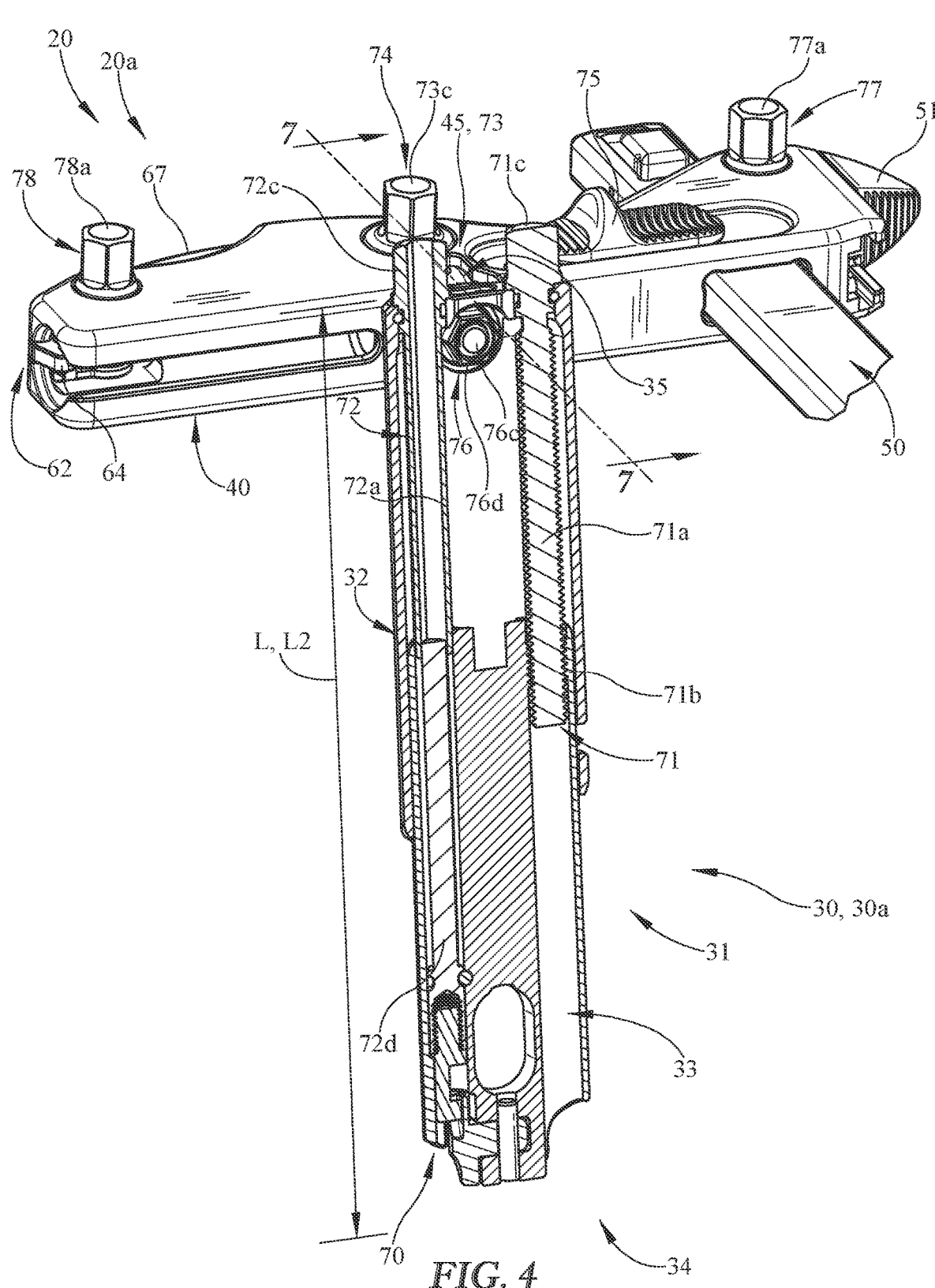
FIG. 4 is a sectional view of the cranial/caudal blade illustrating the cranial/caudal blade extended to a second length longer than the first length.
Figure 5:
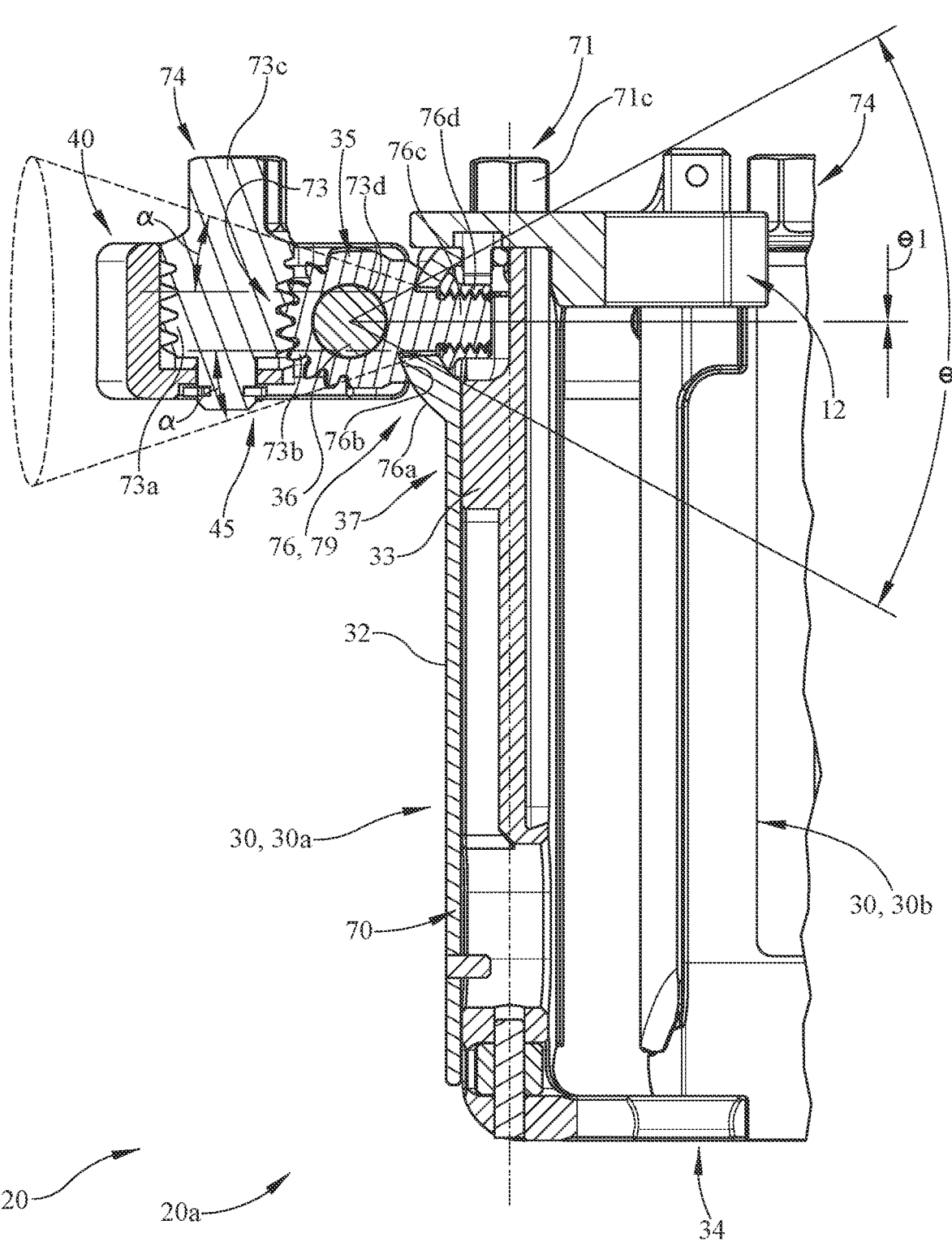
FIG. 5 is a sectional view of the blade and base arm taken along line 5-5 of FIG. 1 illustrating the attachment mechanism therebetween and the first pivoting angle, and illustrating the conical movement between the blade connector and the remaining portion of the blade.
Figure 6:
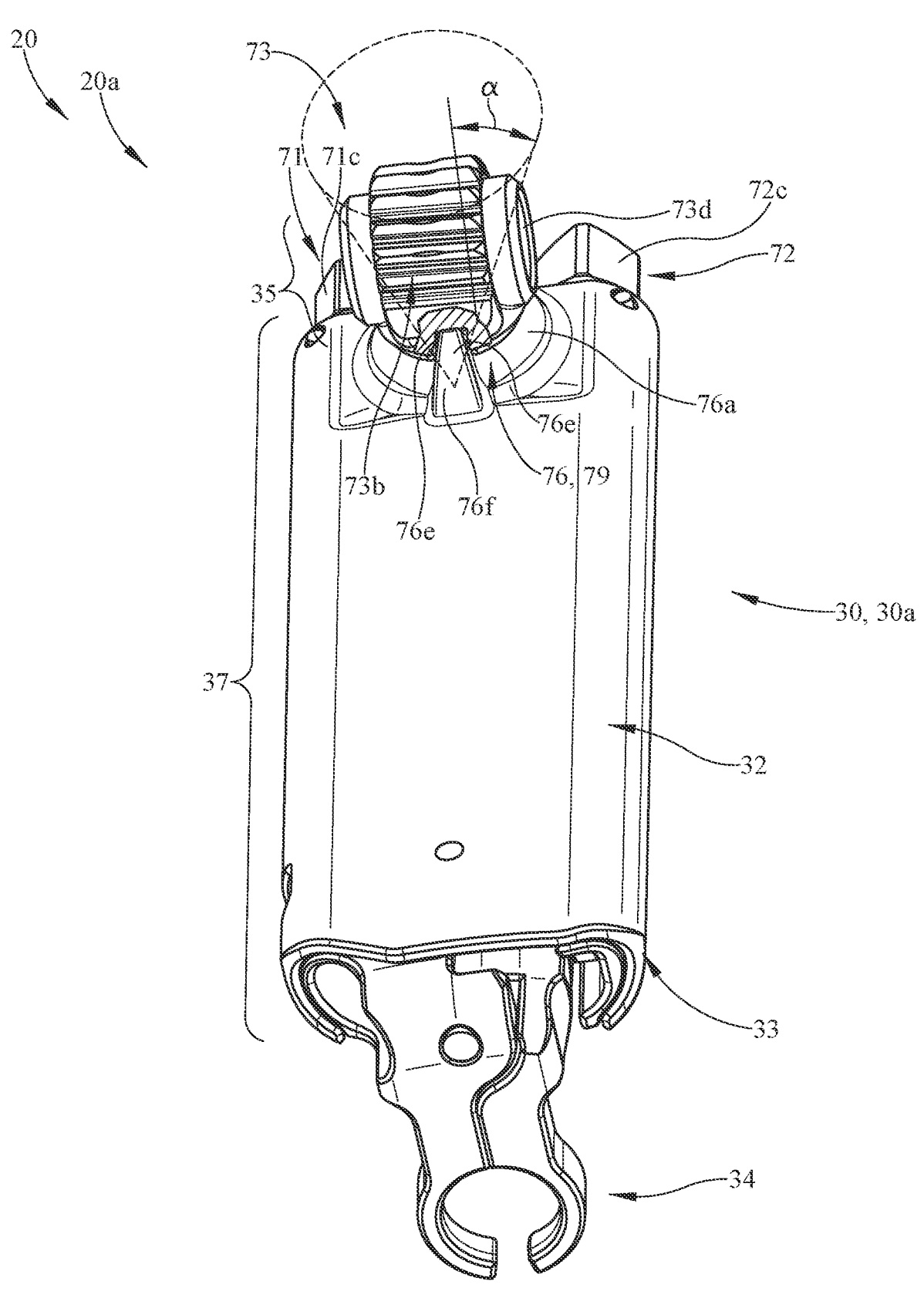
FIG. 6 is a perspective view of the cranial/caudal blade of FIG. 1 illustrating the conical movement between the blade connector and the remaining portion of the blade.
Figure 7:
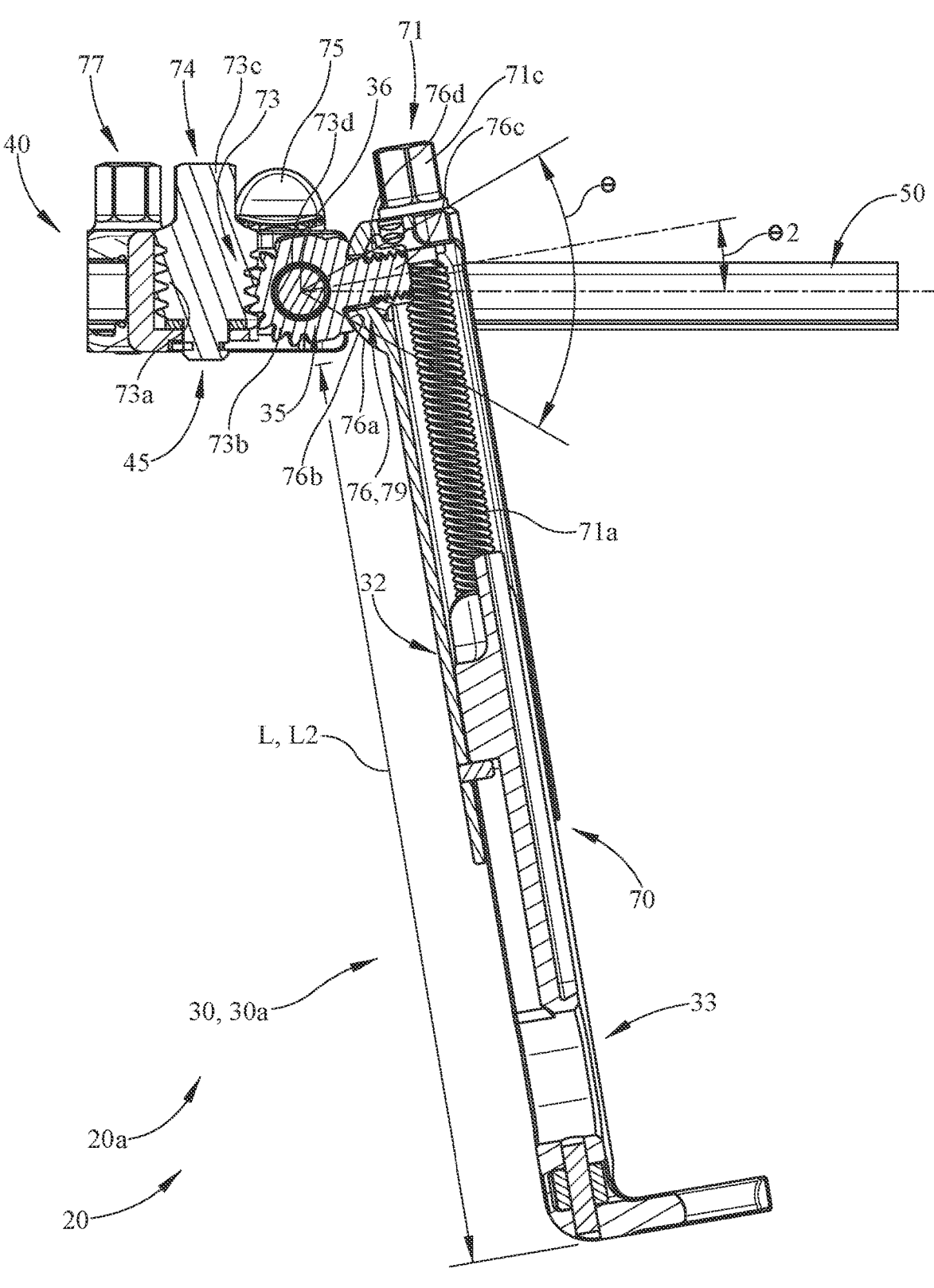
FIG. 7 is a sectional view of the blade and base arm taken along line 7-7 of FIG. 4 illustrating the length varying, or increased length, of the cranial/caudal blade and varying the toe or angle, and illustrating a second pivoting angle larger than the first pivoting angle.
Figure 8:
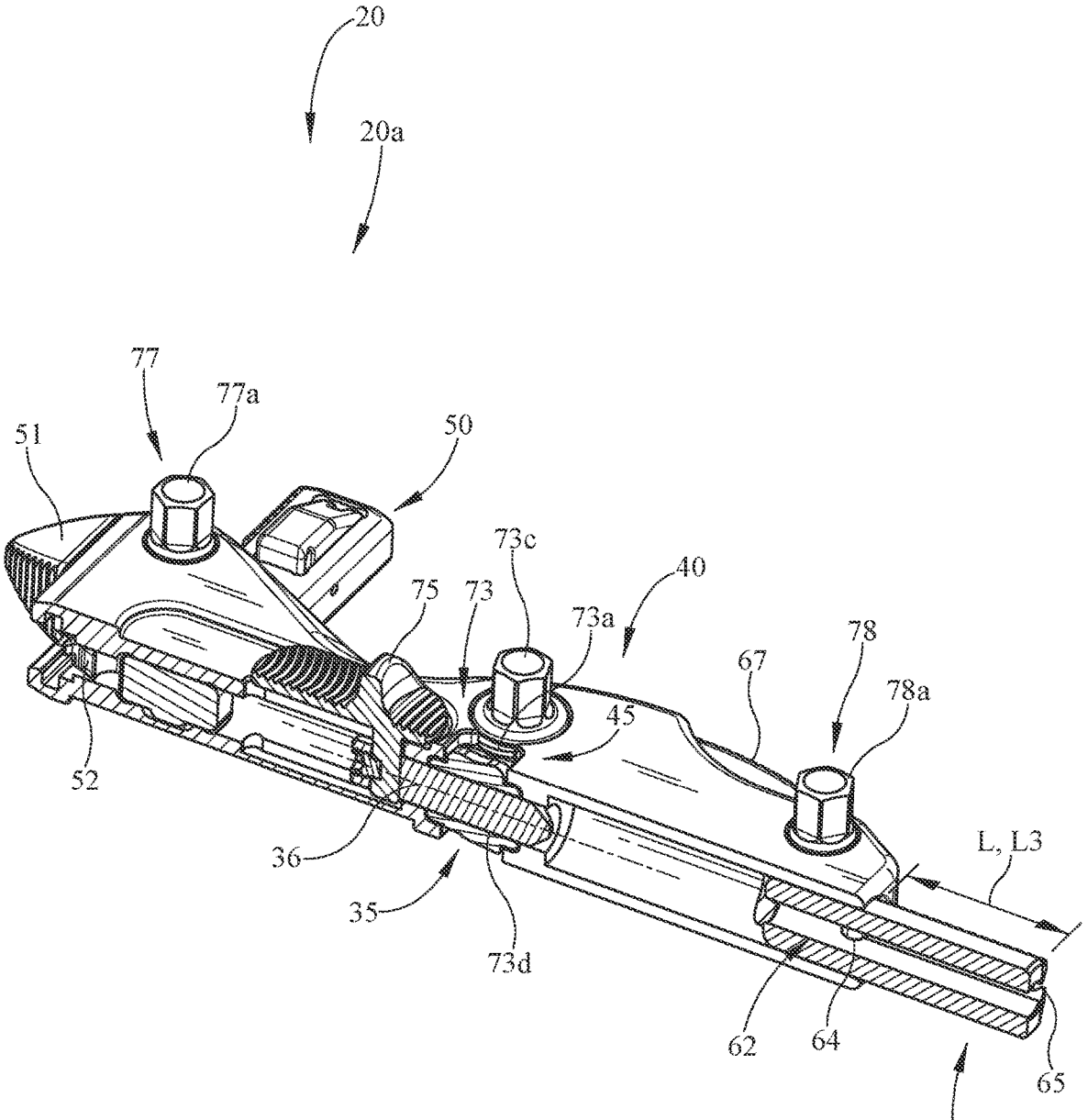
FIG. 8 is a sectional view taken along line 8-8 of FIG. 1 illustrating the stop mechanism and the maximum length of the extension arm from the base arm.

The embodiments of the invention are in the field of retractor manipulation/retracting. In some embodiments, the retractor tool may be a medial-based retractor as shown in the Figures. However, in various embodiments, the retractor tool may be a lateral-based retractor (e.g. lateral blade(s)). In some embodiments, the retractor tool may manipulate at least one first blade by at least one of adjusting a length of the first blade, adjusting a distance between the first blade and a second blade, and/or adjusting an angle between the first blade and a first base arm.

Referring to the Figures, a retractor tool 20 may include one or more blades 30 (e.g. first blade, second blade, third blade, cranial/caudal blade, medial blade, lateral blade, etc.) adjustable relative to the tool frame/body 20a, or one or more portions thereof (e.g. base rack 50, base arm(s) 40, extension arm(s) 60, screw(s) 10, blade(s) 30, implants, and/or alignment clip(s) 12, etc.). The blade 30 may be at least one cranial/caudal blade 30a. The blade 30 may be at least one medial/lateral blade 30b. In the one embodiment shown, two opposing cranial/caudal blades 30a and/or one or more medial blades, if used, may be used in some applications. One or more extension arms 60 may be used in some embodiments.

In some implementations, the one or more blades 30 (e.g. 30a, 30b) may be adjustable in length between a variety of lengths or body lengths L (e.g. first). The blade 30 may expand and/or collapse between a first length L1 and a second length L2, wherein the second length L2 may be larger than the first length L1. The blade 30 or body 31 of the blade may include an upper blade/portion 32 and a lower blade/portion 33. The upper blade 32 or proximal end of the blade 30 may be proximal the base/extension arm and the lower blade 33 or distal end of the blade 30 may be distal from the base/extension arm, adjacent the screw 10 and/or claw 34. In some embodiments, the upper blade 32 or proximal end may include a connector 35 (e.g. second) to engage the base arm 40 or connector 45 (e.g. first). As shown in the one embodiment in FIGS. 1-5, the blade 30 includes a telescoping engagement 70 or telescopes between the first length L1 and the second length L2. More specifically, the upper blade 32 may telescope or slide (e.g. engagement) relative to the lower blade 33 to adjust the length L of the blade (30a, 30b, etc.). Telescoping may include driving the lower blade 33 away from and/or towards the upper blade 32. The lower blade 33 may slide within the upper blade 32. In some embodiments, the blade 30 or tool 20 may include a drive mechanism 71 (e.g. first) to drive or adjust the length L (e.g. increase and/or decrease the length) of the blade 30. The drive mechanism 71 may include a threaded engagement between the upper blade and lower blade. The threaded engagement or upper blade may include a threaded member 71a extending along the length or longitudinal axis and axially held within the upper blade 32 while allowing rotation. The threaded member 71a engages the internal threads or threaded opening/member 71b of the lower blade 33 to position/slide the lower blade 33 to or from the upper blade 32. A tool or other device may engage a blade telescoping hex or drive end 71c of the threaded member 71a. In some embodiments, the blade 30 may include a screw engagement mechanism 72. In the one embodiment shown in FIGS. 1-7, the screw engagement mechanism 72, if used, may be a claw 34 releasably engaging the screw 10 or portions thereof. The claw or claw member 34 thereof may pivot to grasp the screw 10 or reduce the size of the opening therein. The opening may be increase to receive the screw 10, or portions thereof. The claw 34 may be pivoted by a claw hex or drive end 72c positioned on the upper blade 32 or proximal end. A shaft 72a may extend from the claw hex 72c to the claw member(s) 34. The shaft 72a and claw member 34 may pivot about the axis of the elongated shaft relative to the blade 30. In some embodiments where the blade telescopes in length L, the shaft 72a may include an upper shaft 72b and a lower shaft 72d. The lower shaft 72d telescopes/slides relative to the upper shaft 72b to adjust in length corresponding to the change of length of the blade 30. The lower shaft 72d may be keyed or rotationally locked to the upper shaft 72b to lock their rotation/pivot together to pivot the claw 34 (shown in broken lines in FIG. 1) but still allows sliding therebetween when and if the blade 30 telescopes. In use, one or more blades 30, 30a, 30b may telescope to a variety of lengths to change/vary the accessibility to/from the work space or opening defined by the retractor tool, or portions thereof. For example, as shown in the one embodiment in FIG. 1, the user may tilt the tool 20 or frame 20a (e.g. first base arm relative to the second base arm) by adjusting one of the cranial/caudal blades 30a (e.g. first, right) to a longer length L2 than the other/opposing cranial/caudal blades 30a at length L1 (e.g. second, left) to access an area of the work space different from when the opposing blades were parallel in elevation or of the same length. Further, the adjustable blades, if used, may reduce the total number of fixed length blades previously used for the corresponding lengths. For example, one adjustable length blade 30 (e.g. adjustable between 35-55 mm) as shown in the one embodiment may be used instead of a fixed length blade for each one of the blades measuring 35 mm, 40 mm, 45 mm, 50 mm, and 55 mm in length.

In some implementations, the one or more blades 30 (e.g. 30a, 30b) may be adjustable (e.g. pivotable) between a variety of angles θ. The blade 30 may be angled between a variety of angles in at least one plane. In the one embodiment shown in FIGS. 5 and 7, the plane may be in the vertical direction or perpendicular to the top or horizontal plane of the tool 20, or portions thereof (e.g. base arm 40, pin 36). The vertical plane may also be perpendicular to the plane along the length of the base arm 40 in some embodiments. The angle θ between at least one blade and the base arm may be adjusted. The angle may be adjustable (e.g. toe-in, toe-out, toe negative direction, toe positive direction, increasing the work space, decreasing the work space, etc.) between at least one first angle and at least one second angle. As shown in the one embodiment in FIG. 5, the angle θ may be a first angle θ1, such that the first angle θ1 is zero degrees or horizontal. As shown in the one embodiment in FIG. 7, the angle θ may be a second angle θ2, such that the second angle θ2 is about 35 degrees above the horizontal. The one or more blades 30 may angle or pivot in and/or out from the base arm 40. In some embodiments, the angle θ may be in the range of about 50 degrees above the horizontal to about 50 degrees below the horizontal or plane of the base arm. In some embodiments, the range may be about 45 degrees above the horizontal to about 45 degrees below the horizontal or plane of the base arm. The one or more blades 30 may pivot about an axis/pin 36 and/or connector 35, 45. The pin 36 may be a locking pin to releasably engage the blade 30 (e.g. connector 35). The blade or tool may include a tilting/toe/pivoting engagement 73 between the base arm 40, or portion thereof, (e.g. first connector 45) and the blade 30, or portion thereof (e.g. second connector 35). The pivoting engagement 73 may allow the blade 30 to angle or pivot in and/or out from the base arm 40. The pivoting engagement 73 may be one or more gears engaging between the base arm and blade. In the one embodiment shown in the Figures, pivoting engagement 73, the base arm 40, or first connector 45 may include one or more worm gears 73a (e.g. teeth, thread) and/or pin 36 and the pivoting engagement 73, blade 30, or second connector 35 may include a worm wheel 73b (e.g. teeth) and/or through opening 73d. The worm wheel 73b may include a through opening receiving the pin 36. The pivoting engagement 73, tool 20, blade 30, or base arm 40 may include a drive mechanism 74 (e.g. second, worm gear) to operate or drive the pivoting engagement 73. A tool or other device may engage a blade toe hex or drive end 73c of the worm gear 73a. The worm gear 73a of the base arm 40 rotates/engages the worm wheel 73b or teeth to position/angle/pivot the blade (e.g. connector, upper, lower) both in and out from the base arm. A locking mechanism 75, such as a slider/pin 36 of the base arm as shown in the one embodiment, may releasably lock the worm wheel 73b/connector 35/blade 30 into engagement with the worm gear 73a/connector 45/base arm 40.

In some implementations, the tool 20 or at least one blade 30 may include one or more flexible adjustment mechanisms 76 for adjusting the connector 35 of the blade 30 relative to a remaining portion 37 of the blade. The flexibility may allow for easier assembly or engagement of the blade/connector (e.g. worm wheel, teeth) to the base arm/connector (e.g. worm gear, thread). For example, the blades may not have to be orientated parallel or aligned to assemble. Further, the increased movement and flexibility of the blade 30 may be useful during use. The flexible adjustment mechanism 76, if used, may be a joint 79 that allows the blade connector 35 to move relative to the remaining portion 37 of the blade 30 (e.g. upper blade, lower blade). The joint 79/engagement 76 between the connector 35 of the blade 30 and the remaining portion 37 of the blade may allow conical movement of a variety of angles a between the connector 35 and the remaining portion 37 of the blade. In some embodiments, the joint 79 or flexible adjustment mechanism 76 may allow movement of about 1-12 degrees of conical movement. In some embodiments, the range may be about 2-10 degrees, or more specifically about 2.5 to 3 degrees. As shown in the one embodiment, the joint 79 may allow an angle α of about 3 degrees of conical movement of the blade connector (e.g. worm wheel) relative to the remaining portion of the blade. In some implementations, the angle or range of conical movement may increase as the length of the blade decreases or decrease as the length of the blade increases. For example, a 35-55 mm blade may have about a 10 degree angle of movement in some embodiments. Further, for example, a 50-80 mm blade may have about a 7 degree angle of movement in some embodiments. As shown in the one embodiment in FIGS. 5 and 6, the joint 79 (e.g. socket, flexible adjustment mechanism) may include a spherical outer/inner periphery 76a of the blade (e.g. upper blade) engaging a spherical member 76b of the connector 35. A threaded end 76c of the connector may extend through an opening in the blade and be secured by a nut 76d (e.g. spherical shaped periphery). If used, the blade 30/connector 35/spherical member 76b may include a slot 76e receiving a key or stop 76f of the blade wall (e.g. upper blade, remaining portion), or vice versa, to reduce or prevent turning or twisting of the connector relative to the blade when engaged/aligned (e.g. hard stop).

Figures 9A, 9B, 9C:
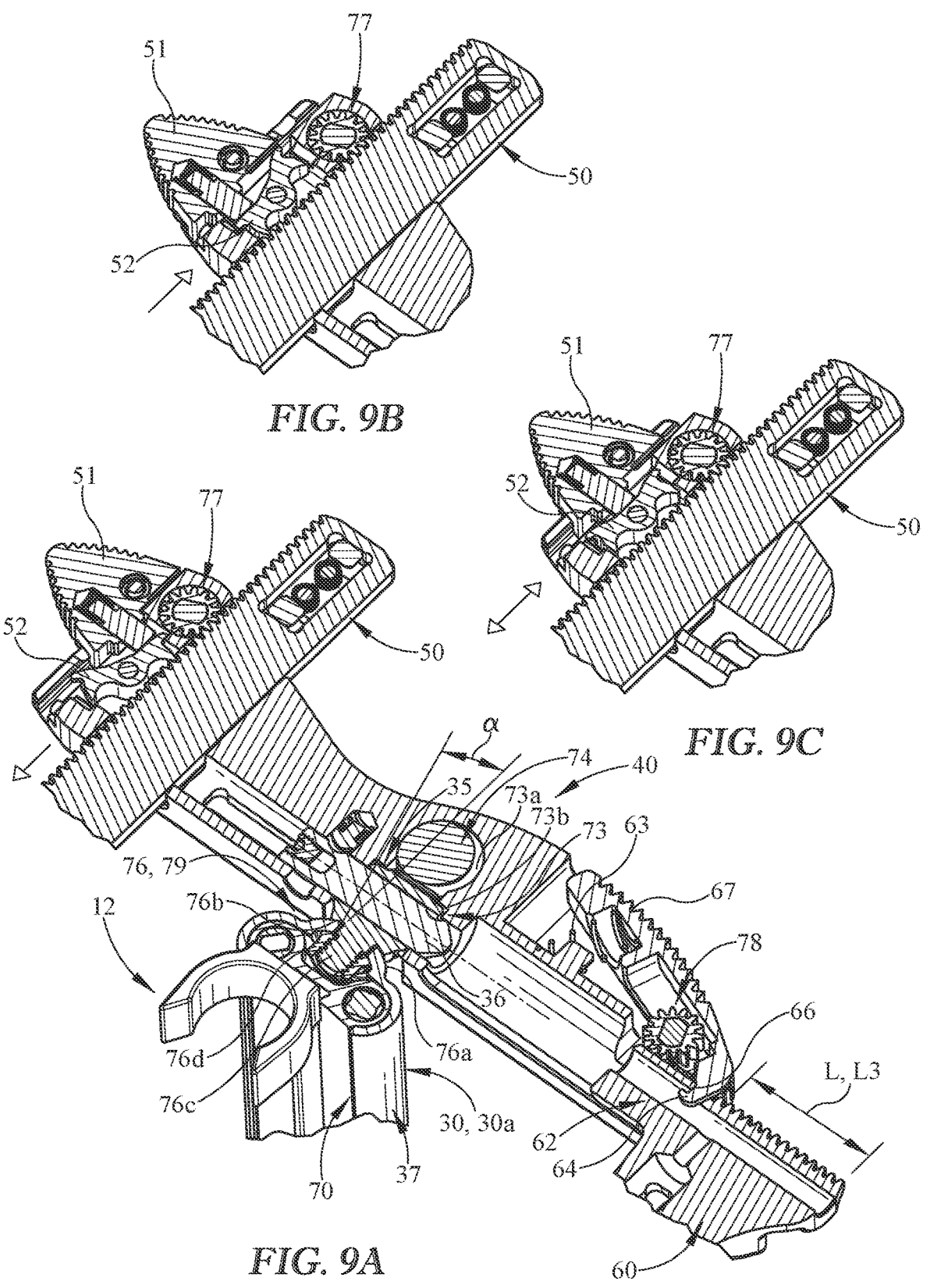
FIG. 9A is a sectional view taken along line 9-9 of FIG. 1 illustrating the stop mechanism and the maximum length of the extension arm and the drive mechanism of the base arm in a contraction mode.
FIG. 9B is an enlarged sectional view of FIG. 9A illustrating the drive mechanism of the base arm in a distraction mode.
FIG. 9C is an enlarged sectional view of FIG. 9A illustrating the drive mechanism of the base arm in an unlocked mode.

In some implementations, a distance D between one or more blades 30 may be adjusted therebetween. The distance D between two blades 30 (e.g. two opposing cranial/caudle blades, medial/lateral blade and cranial/caudle blade, etc.) may be adjusted therebetween. For example, the distance D may be adjusted along the base rack 50. The tool 20/base arm 40/blade 30 may include a rack slider 51. The rack slider 51 may allow the user to select the mode or movement of the one or more base arms. The rack slider 51 may pivot the rocker arm 52 into and out of engagement with the rack corresponding to the selected mode. The rack slider 51 may control the movement of the rack for distraction (FIG. 9B) and/or contraction (FIG. 9A). Further, there may be an unlocked position (FIG. 9C) of the slider to allow free movement (e.g. not controlled) of the base arm along the length of the base rack. In the contraction mode as shown in FIGS. 1 and 9A, a rocker arm 52, positioned about a pivot/hinge, is urged/wedged/biased into the teeth of the base rack 50 to allow controlled contraction by the drive mechanism 77 or to decrease the distance D. Further, distraction or movement in the other direction may not be used in some embodiments when in the contraction mode. In the distraction mode as shown in FIG. 9B, a rocker arm 52 is urged/wedged/biased into the teeth of the base rack 50 to allow controlled distraction by the drive mechanism 77 or to increase the distance D. Further, contraction or movement in the other direction may not be used in some embodiments when in the distraction mode. In the unlocked mode as shown in FIG. 9C, the rocker arm 52 is disengaged from the teeth of the base rack 50 to allow free movement. The drive mechanism 77, if used, may increase and/or decrease the distance D when in the unlocked mode. When contracting and/or distracting the opposing base arms (e.g. first, second) and/or blades, the movement is controlled and driven by a drive mechanism 77 (e.g. third). The drive mechanism 77 may both contract and distract the distance between two of the blades in some embodiments. The drive mechanism 77 (e.g. third), if used, may be a base arm hex or drive member 77a to drive the base arm 40 and/or blade along the length of the base rack 50 during at least one of the modes.

In some implementations, the tool 20/blade 30/base arm 40 may include a medial/lateral extension arm 60. The extension arm 60, if used, may extend from at least one base arm 40 for a variety of lengths L. The variety of lengths L of the extension arm 60 projecting from the base arm 40 may vary the overall length of the combined base arm 40 and extension arm 60 and/or define a variety of work spaces (e.g. shapes, sizes). The medial blade 30b, if used, may also be moved to a variety of distances D with the extension arm 60 from the cranial/caudal blade(s) 30a and/or base rack 50 by varying the length L of the extension arm. The tool/blade/base arm/extension may include a catch or stop mechanism 62 in some embodiments. The catch/stop mechanism 62 may lock/stop the extension arm 60 relative to the base arm 40 at one or more lengths L (e.g. predetermined) or prevent the extension arm from further extension. The catch 62 may stop the extension arm 60 extending from the base arm 40 at the predetermined length L3 of the variety of lengths. The catch 62 may prevent the extension arm 60 from falling away or separating from the base arm 40 at a maximum extension length or predetermined length L3 (e.g. first, maximum length) as shown in FIG. 9A. The catch 62 may include a biasing mechanism 63 urging a latch 64 into a slot 65 of the extension arm 60. The latch 64 slides within the slot 65 for a variety of lengths L. To prevent separation between the base arm and the extension arm, the latch 64, if used, engages/abuts the end 66 of the slot 65 (e.g. at the maximum extension length L3) to not allow further extension/separation/length. A release button 67, if used, may be used in some embodiments to release the extension arm 60 from the base arm 40 or overcome the catch 62 (e.g. remove the latch from the slot/end) to allow separation. The release button 67 may position the latch 64 out of engagement with the periphery or end 66 defining the slot 65 allowing the extension arm to separate. When increasing and/or decreasing the exposed length of the extension arm relative to the base arm, the movement is controlled and driven by a drive mechanism 78 (e.g. fourth). The drive mechanism may increase and/or decrease the length of the extension arm or combined extension arm and base arm in some embodiments. The drive mechanism 78 (e.g. fourth), if used, may be an extension arm hex or drive member 78a to drive the extension arm in one or more directions relative to the base arm. The drive mechanisms (e.g. first, second, third, fourth, etc.), if used, may include a rack and pinion as shown in the one embodiment.

In some embodiments, the retractor tool and/or design may be designed to work with pedicle screws and/or implants. In various embodiments, the retractor tool may be designed to work with a specific type of screw, such as the Mariner pedicle screws. In various embodiments, the retractor tool includes a claw design to fit the geometry of Mariner pedicle screws. In some embodiments, the rigidity of the retractor may be improved. In some embodiments, one or more gears and/or teeth may tie components together for rigidity. In various embodiments, the retractor blades contract and/or distract. In some embodiments, the retractor indirectly engages with an interbody implant once the implant is in situ. In some embodiments, the retractor does not directly touch the implant—the retractor may directly engage with the vertebrae to indirectly compress the interbody implant. In some embodiments, the retractor tool may include controlled toe-in and/or toe-out of the blades via gears. In some embodiments, the retractor tool may include controlled telescoping of the blades via threads, for example for the medial blade and/or cranial/caudal blade.

In addition, in various embodiments, the retractor tool may include one or more floating heads or connectors. This may allow flexibility of in situ adjustment of blade engagement. Further, the floating head or connector may engage with one or more worm gears. This may allow different approach angles, in different planes. This may also make assembly of the modular retractor components much easier. In various embodiments, the retractor tool may include one or more table arm locks. This may help to fix the retractor and/or apply a force to move the vertebrae in a spondylolisthesis adjustment. In some embodiments, the retractor tool may include cranial/caudal blades. In various embodiments, the retractor tool may include one or more external light sources (e.g. such as a light tube).

In various embodiments, the Contraction-Unlocked-Distraction Mode Simplification may be used. In some embodiments, these modes may be more intuitive to the user. In some embodiments, the retractor tool may include sliding auto-locks. In various embodiments, the lock spring may be loaded so that it can auto-latch or lock when the blades are mated with the gears. In various embodiments, the retractor tool may include additional blade sizes. Providing more blade sizes may allow a decrease in the max telescoping range of each blade. Providing more blade sizes may be less cumbersome for the user; less change of binding in a free-floating design. In some embodiments, the retractor tool may include a light attachment piece. The light attachment piece may permit the user to dock proximally (e.g. top of retractor). In various embodiments, the retractor tool may include a medial blade free-floating telescoping. In some embodiments, the color of the handle of the medial blade inserter may be changed. For example, blue to orange. In addition, in some embodiments, the claw hex interface with wrench may be changed to prevent or reduce accidental use during operation.

While several embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

It is to be understood that the embodiments are not limited in its application to the details of construction and the arrangement of components set forth in the description or illustrated in the drawings. The invention is capable of other embodiments and of being practiced or of being carried out in various ways. Unless limited otherwise, the terms "connected," "coupled," "in communication with," and "mounted," and variations thereof herein are used broadly and encompass direct and indirect connections, couplings, and mountings. In addition, the terms "connected" and "coupled" and variations thereof are not restricted to physical or mechanical connections or couplings.

The invention claimed is:

1. A retractor tool comprising:
   two or more blades adjustable in length, wherein:
      at least one blade comprises an upper blade and a lower blade;
      the upper blade further comprises an upper shaft having a shaft wall defining a hollow, the lower blade further comprises a lower shaft, the hollow configured to receive the lower blade to allow the lower shaft to move along a longitudinal direction of the upper shaft; and the upper blade further comprises an opening at an upper end, the lower blade further comprises a lower threaded member, the opening is configured to receive an upper threaded member to engage with the lower threaded member to position or slide the lower blade to or from the upper blade;

two or more base arms, the two or more blades mechanically engaged to the two or more base arms respectively;

a base rack, the two or more base arms slideably coupled to the base rack;

wherein the two or more base arms are configured to slide along a longitudinal direction of the base rack to adjust a distance between the two or more blades.

2. The retractor tool of claim 1 wherein at least one of the two or more blades telescopes between a first length and a second length longer than the first length.

3. The retractor tool of claim 2 wherein the upper blade and the lower blade telescope relative to each other.

4. The retractor tool of claim 1 wherein at least one of the two or more blades is a medial blade and/or a cranial/caudal blade.

5. The retractor tool of claim 1 further comprising a pivoting engagement between one of the base arms and one of the two or more blades, wherein the pivoting engagement allows one of the two or more blades to angle both in and out from the base arms.

6. The retractor tool of claim 1 wherein at least one of the two or more blades includes a joint allowing a first portion of the at least one of the two or more blades to move relative to a second portion of the at least one of the two or more blades, wherein the first portion is a connector engaging one of the base arms and the second portion is a remaining portion of the at least one of the two or more blades.

7. The retractor tool of claim 1 further including a first drive mechanism to both decrease and increase the length of at least one of the two or more blades.

8. The retractor tool of claim 1, wherein the base rack includes a distance drive mechanism to both contract and distract a distance between two of the two or more blades.

9. The retractor tool of claim 1 further including an extension arm extending from one of the base arms for a variety of lengths, and a catch stopping the extension arm extending from the one of the base arms at a predetermined length of the variety of lengths.

10. A retractor tool comprising:
a base arm;
at least one blade; and
a pivoting engagement between the base arm and the at least one blade, wherein the pivoting engagement comprises a gear end, a thread end, and a through opening, the gear end is configured to be engaged with a driving mechanism, the thread end is engaged with the at least one blade, the through opening is configured to receive a pin engaged with the base arm, such that an up or down movement of the driving mechanism drives the pivoting engagement to rotate about the pin, allowing the at least one blade to angle both in and out from the base arm.

11. The retractor tool of claim 10 further comprising the drive mechanism to operate the pivoting engagement.

12. The retractor tool of claim 10 wherein the at least one blade includes a joint between a connector and a remaining portion of the at least one blade, wherein the joint allows conical movement between the connector and the remaining portion of the at least one blade.

13. The retractor tool of claim 12 wherein the remaining portion of the at least one blade includes an upper blade and a lower blade, wherein the lower blade telescopes relative to the upper blade.

14. The retractor tool of claim 13, wherein the upper blade further comprises an opening at an upper end, the lower blade further comprises a lower threaded member, the opening is configured to receive an upper threaded member to engage with the lower threaded member to position or slide the lower blade to or from the upper blade.

15. The retractor tool of claim 13, wherein:
the upper blade further comprises an upper shaft having a shaft wall defining a hollow;
the lower blade further comprises a lower shaft; and
the hollow is configured to receive the lower blade to allow the lower shaft to move along a longitudinal direction of the upper shaft.

16. The retractor tool of claim 10 wherein the pivoting engagement includes the base arm having a worm gear and the at least one blade having a worm wheel.

17. The retractor tool of claim 10 further comprising an extension arm extending from the base arm for a variety of lengths, and a catch stopping the extension arm extending from the base arm at a predetermined length of a variety of lengths.

* * * * *